(12) United States Patent
McLean et al.

(10) Patent No.: US 7,106,523 B2
(45) Date of Patent: Sep. 12, 2006

(54) OPTICAL LENS USED TO FOCUS LED LIGHT

(75) Inventors: Bruce S. McLean, Sandy, UT (US); Vasiliy Nosov, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 37 days.

(21) Appl. No.: 10/044,346

(22) Filed: Jan. 11, 2002

(65) Prior Publication Data

US 2003/0133203 A1 Jul. 17, 2003

(51) Int. Cl.
| G02B 3/02 | (2006.01) |
| G02B 13/08 | (2006.01) |
| G02B 13/18 | (2006.01) |
| A61C 1/00 | (2006.01) |
| A61C 9/00 | (2006.01) |

(52) U.S. Cl. .................. 359/708; 359/719; 433/29; 433/37

(58) Field of Classification Search .......... 359/708, 359/710, 712, 718, 719, 717; 433/29, 37, 433/126

See application file for complete search history.

(56) References Cited

U.S. PATENT DOCUMENTS

| 3,310,358 A | 3/1967 | Marcatili |
| 3,704,928 A | 12/1972 | Coombs et al. |
| 3,930,149 A | 12/1975 | French |
| 4,184,196 A | 1/1980 | Moret et al. |
| 4,221,994 A | 9/1980 | Friedman et al. |
| 4,229,658 A | 10/1980 | Gonser |
| 4,245,890 A | 1/1981 | Hartman et al. |
| 4,266,535 A | 5/1981 | Moret |
| 4,281,366 A | 7/1981 | Wurster et al. ............... 362/32 |
| 4,309,617 A | 1/1982 | Long |
| 4,348,180 A | 9/1982 | Schuss |
| 4,392,827 A | 7/1983 | Martin |
| 4,522,594 A | 6/1985 | Stark et al. |
| 4,611,992 A | 9/1986 | Lokken |
| 4,666,405 A | 5/1987 | Ericson |
| 4,666,406 A | 5/1987 | Kanca, III |
| 4,682,950 A | 7/1987 | Dragan |
| 4,698,730 A | 10/1987 | Sakai et al. |

(Continued)

FOREIGN PATENT DOCUMENTS

WO WO 99/35995 7/1999

OTHER PUBLICATIONS

"Dental/Medical Diagnostic Systems, Inc. Received $4.0 Million Order for Its Wireless Apollo e and Wavelight Curing Units Based on New LED Technology", ww.compoundsemiconductor.net (Nov. 20, 2000).

"LUXoMAX the Latest News from Akeda Dental", Akeda Dental A/S, www.akeda.dk (Oct. 1, 2001).

*Primary Examiner*—Georgia Epps
*Assistant Examiner*—Alicia M Harrington
(74) *Attorney, Agent, or Firm*—Workman Nydegger

(57) ABSTRACT

An aspheric lens focuses light emitting from a light-emitting diode (LED) of a light-generating dental device for curing light-curable compounds during dental procedures. The LED is preferably affixed to the end of an extension arm extending away from a light-generating dental device. A transparent shield, which is removably attachable to the extension arm, protects the aspheric lens from physical contact during use. The aspheric lens, which has a flat end and an aspheric end, is held in place by the extension arm and/or the transparent shield with the flat end of the aspheric lens being held in close proximity to the LED. Light emitted from the LED enters the flat end of the lens and exists the aspheric end of the lens, which focuses the light for curing light-curable compounds during dental procedures.

26 Claims, 4 Drawing Sheets

U.S. PATENT DOCUMENTS

| | | |
|---|---|---|
| 4,733,937 A | 3/1988 | Lia et al. |
| 4,836,782 A | 6/1989 | Gonser |
| 4,935,665 A | 6/1990 | Murata |
| 4,948,215 A | 8/1990 | Friedman |
| 4,963,798 A | 10/1990 | McDermott |
| 4,992,045 A | 2/1991 | Beisel |
| 5,013,144 A | 5/1991 | Silverglate et al. |
| 5,013,240 A | 5/1991 | Bailey et al. |
| 5,017,140 A | 5/1991 | Ascher |
| 5,043,634 A | 8/1991 | Rothwell, Jr. et al. |
| 5,071,222 A | 12/1991 | Laakmann et al. |
| 5,115,761 A | 5/1992 | Hood |
| 5,123,845 A | 6/1992 | Vassiliadis et al. |
| 5,139,495 A | 8/1992 | Daikuzono |
| 5,161,879 A | 11/1992 | McDermott |
| 5,275,564 A | 1/1994 | Vassiliadis et al. |
| 5,285,318 A | 2/1994 | Gleckman |
| 5,288,231 A | 2/1994 | Kuehn et al. |
| 5,290,169 A | 3/1994 | Friedman et al. |
| 5,312,249 A | 5/1994 | Kennedy |
| 5,328,368 A | 7/1994 | Lansing et al. |
| 5,348,552 A | 9/1994 | Nakajima et al. |
| 5,371,826 A | 12/1994 | Friedman |
| 5,382,799 A | 1/1995 | May |
| 5,388,988 A | 2/1995 | Goisser et al. |
| 5,397,892 A | 3/1995 | Abdelqader |
| 5,415,543 A | 5/1995 | Rozmajzl, Jr. |
| 5,420,768 A | 5/1995 | Kennedy |
| D361,382 S | 8/1995 | Brunsell et al. |
| 5,448,323 A | 9/1995 | Clark et al. |
| 5,457,611 A | 10/1995 | Verderber |
| 5,485,317 A | 1/1996 | Perissinotto et al. ........ 359/712 |
| 5,521,392 A | 5/1996 | Kennedy et al. |
| 5,527,261 A | 6/1996 | Monroe et al. |
| 5,616,141 A | 4/1997 | Cipolla |
| 5,634,711 A | 6/1997 | Kennedy et al. ............ 362/119 |
| 5,660,461 A | 8/1997 | Ignatius et al. |
| 5,669,769 A | 9/1997 | Disel |
| D385,051 S | 10/1997 | Wu |
| D385,630 S | 10/1997 | Lieb et al. |
| 5,698,866 A | 12/1997 | Doiron et al. |
| 5,711,665 A | 1/1998 | Adam et al. |
| 5,733,029 A | 3/1998 | Monroe |
| 5,749,724 A | 5/1998 | Cheng |
| 5,759,032 A | 6/1998 | Bartel |
| 5,762,605 A | 6/1998 | Cane et al. |
| 5,768,458 A | 6/1998 | Ro et al. |
| 5,772,643 A | 6/1998 | Howell et al. |
| 5,782,553 A | 7/1998 | McDermott |
| 5,791,898 A | 8/1998 | Maissami |
| 5,797,740 A | 8/1998 | Lundvik |
| 5,803,729 A | 9/1998 | Tsimerman |
| 5,880,839 A | 3/1999 | Ishizuka et al. |
| 5,885,082 A | 3/1999 | Levy |
| 5,905,268 A | 5/1999 | Garcia et al. |
| 5,908,295 A | 6/1999 | Kawata |
| 5,912,470 A | 6/1999 | Eibofner et al. |
| 5,921,777 A | 7/1999 | Dorman |
| 5,971,755 A | 10/1999 | Liebermann et al. |
| 5,975,895 A | 11/1999 | Sullivan |
| 6,001,058 A | 12/1999 | Sano et al. |
| 6,008,264 A | 12/1999 | Ostler et al. |
| 6,019,482 A | 2/2000 | Everett |
| 6,019,599 A | 2/2000 | Völcker et al. |
| 6,028,694 A | 2/2000 | Schmidt |
| 6,033,087 A | 3/2000 | Shozo et al. |
| 6,033,223 A | 3/2000 | Narusawa et al. |
| 6,036,336 A | 3/2000 | Wu |
| 6,059,421 A | 5/2000 | White et al. |
| 6,068,474 A | 5/2000 | Senn et al. |
| 6,077,073 A | 6/2000 | Jacob |
| 6,086,366 A | 7/2000 | Mueller et al. |
| 6,089,740 A | 7/2000 | Forehand et al. |
| 6,095,661 A | 8/2000 | Lebens et al. |
| 6,095,812 A | 8/2000 | Senn et al. |
| 6,099,520 A | 8/2000 | Shimoji ........................ 606/2 |
| 6,102,696 A | 8/2000 | Osterwalder et al. |
| 6,103,203 A | 8/2000 | Fischer |
| 6,123,545 A | 9/2000 | Eggler et al. |
| 6,155,823 A | 12/2000 | Nagel |
| 6,159,005 A | 12/2000 | Herold et al. ................. 433/29 |
| 6,200,134 B1 | 3/2001 | Kovac et al. ................. 433/29 |
| 6,208,788 B1 * | 3/2001 | Nosov ........................ 385/121 |
| 6,270,343 B1 | 8/2001 | Martin |
| 6,280,187 B1 | 8/2001 | Stone |
| 6,282,013 B1 | 8/2001 | Ostler et al. |
| 6,318,996 B1 | 11/2001 | Melikechi et al. |
| 6,322,358 B1 | 11/2001 | Senn et al. |
| 6,325,623 B1 | 12/2001 | Melnyk et al. |
| 6,328,456 B1 | 12/2001 | Mize |
| 6,331,111 B1 | 12/2001 | Cao |
| 6,361,192 B1 | 3/2002 | Fussell et al. |
| 6,361,489 B1 | 3/2002 | Tsai |
| 6,398,398 B1 | 6/2002 | Moschkowitz |
| 6,402,511 B1 * | 6/2002 | Calderwood ................. 433/29 |
| 6,417,917 B1 | 7/2002 | Jung et al. |
| 6,419,483 B1 | 7/2002 | Adam et al. |
| 6,439,888 B1 | 8/2002 | Boutoussov et al. |
| 6,465,961 B1 | 10/2002 | Cao |
| 6,468,077 B1 | 10/2002 | Melikechi et al. |
| 6,478,447 B1 | 11/2002 | Yen |
| 6,482,004 B1 | 11/2002 | Senn et al. |
| 6,485,301 B1 | 11/2002 | Gemunder et al. |
| 6,511,317 B1 | 1/2003 | Melikechi et al. |
| 6,511,321 B1 | 1/2003 | Trushkowsky et al. |
| 6,514,075 B1 | 2/2003 | Jacob |
| 6,611,110 B1 | 8/2003 | Fregoso |
| 6,692,251 B1 | 2/2004 | Logan et al. |
| 6,692,252 B1 | 2/2004 | Scott |
| 6,709,128 B1 | 3/2004 | Gordon et al. |
| 6,719,558 B1 | 4/2004 | Cao |
| 6,719,559 B1 | 4/2004 | Cao |
| 6,755,648 B1 | 6/2004 | Cao |
| 6,755,649 B1 | 6/2004 | Cao |
| 2001/0038992 A1 | 11/2001 | Otsuka |
| 2001/0046652 A1 | 11/2001 | Ostler et al. |
| 2001/0055451 A1 | 12/2001 | Kuhara et al. |
| 2002/0073921 A1 | 6/2002 | Russell et al. |
| 2002/0085372 A1 * | 7/2002 | Lehrer ........................ 362/105 |
| 2002/0093833 A1 | 7/2002 | West |
| 2002/0102513 A1 | 8/2002 | Plank |
| 2002/0115037 A1 | 8/2002 | Cao ............................. 433/29 |
| 2002/0133970 A1 | 9/2002 | Gordon et al. ................ 34/250 |
| 2002/0163317 A1 | 11/2002 | Cao ............................ 315/291 |
| 2002/0167283 A1 | 11/2002 | Cao ............................ 315/291 |
| 2002/0168603 A1 | 11/2002 | Cao ............................. 433/29 |
| 2002/0168604 A1 | 11/2002 | Cao ............................. 433/29 |
| 2002/0168605 A1 | 11/2002 | Cao ............................. 433/29 |
| 2002/0168606 A1 | 11/2002 | Cao ............................. 433/29 |
| 2002/0168607 A1 | 11/2002 | Cao ............................. 433/29 |
| 2002/0168608 A1 | 11/2002 | Cao ............................. 433/29 |
| 2002/0172912 A1 | 11/2002 | Cao ............................. 433/29 |
| 2002/0172913 A1 | 11/2002 | Cao ............................. 433/29 |
| 2002/0172914 A1 | 11/2002 | Cao ............................. 433/29 |
| 2002/0172915 A1 | 11/2002 | Cao ............................. 433/29 |
| 2002/0172916 A1 | 11/2002 | Cao ............................. 433/29 |
| 2002/0172917 A1 | 11/2002 | Cao ............................. 433/29 |
| 2002/0175352 A1 | 11/2002 | Cao ............................ 257/258 |
| 2002/0175628 A1 | 11/2002 | Cao ............................. 315/56 |
| 2002/0177095 A1 | 11/2002 | Cao ............................. 433/29 |
| 2002/0177096 A1 | 11/2002 | Cao ............................. 433/29 |

| | | | | | |
|---|---|---|---|---|---|
| 2002/0177099 A1 | 11/2002 | Cao ............................ 433/29 | 2003/0036031 A1 | 2/2003 | Lieb et al. |
| 2002/0180368 A1 | 12/2002 | Cao ........................... 315/149 | 2003/0038291 A1 | 2/2003 | Cao ............................ 257/81 |
| 2002/0181947 A1 | 12/2002 | Cao ........................... 392/409 | 2003/0039119 A1 | 2/2003 | Cao ........................... 362/227 |
| 2002/0182561 A1 | 12/2002 | Cao ............................ 433/29 | 2003/0039120 A1 | 2/2003 | Cao ........................... 362/227 |
| 2002/0182562 A1 | 12/2002 | Cao ............................ 433/29 | 2003/0039122 A1 | 2/2003 | Cao ........................... 362/294 |
| 2002/0187454 A1 | 12/2002 | Melikechi et al. | 2003/0040200 A1 | 2/2003 | Cao ........................... 438/800 |
| 2002/0187455 A1 | 12/2002 | Melikechi et al. | 2003/0081430 A1 | 5/2003 | Becker |
| 2002/0190659 A1 | 12/2002 | Cao ........................... 315/149 | 2003/0152885 A1 | 8/2003 | Dinh |
| 2002/0190660 A1 | 12/2002 | Cao ........................... 315/149 | 2003/0219693 A1 | 11/2003 | Cao |
| 2002/0197582 A1 | 12/2002 | Cao ............................ 433/29 | | | |
| 2003/0001507 A1 | 1/2003 | Cao ............................ 315/56 | * cited by examiner | | |

OPTICAL LENS USED TO FOCUS LED LIGHT

BACKGROUND OF THE INVENTION

1. The Field of the Invention

The present invention generally relates to the field of light curing devices and, more specifically, to light curing dental devices and methods for irradiating and curing photosensitive dental filling compounds.

2. The Relevant Technology

In the field of dentistry, dental cavities are often filled and/or sealed with photosensitive compounds that are cured by exposure to radiant energy, such as visible light. These compounds, commonly referred to as light-curable compounds, are placed within dental cavity preparations or onto dental surfaces where they are subsequently irradiated by light. The radiated light causes photosensitive components within the compounds to polymerize, thereby hardening the light-curable compounds within the dental cavity preparation or another desired location.

Light is typically directed to the light-curable compounds by a light-generating dental device comprising a lamp, such as a halogen lamp bulb, and a light guide, such as a fiber optic wand that can capture some of the light that is generated by the lamp. Special reflectors and filters are typically employed to control the quantity and wavelength of light that is permitted to enter the fiber optic wand. Light traveling through the fiber optic wand is finally dispersed out of a tip at a desired location within a patient's mouth.

One problem with existing LED light-generating devices, as well as with other light-generating devices which incorporate lamps, is they require a fiber optic wand to carry the light emitted by the lamp from within the light-generating device to the application site where the light is finally directed to a desired location. Light-generating devices may be manufactured with integrated fiber optic wands or sold with separate and detachable fiber optic wands. Although fiber optic wands are useful for their intended purposes, they are undesirable because they add to the cost of equipment, and hence to the total cost for performing dental procedures with light-curable compounds Another problem with existing light-generating devices is that they are not very efficient. In particular, a large quantity of radiation energy is lost due to filtering, dissipated light, and light that is not reflected and properly channeled into the fiber optic wand. This is a problem because it generally results in increased power requirements for generating a desired output of radiation. Another problem is that complicated cooling systems are required to compensate for the heat that is generated by unchanneled and unused light, such as the light that is absorbed by special filters, reflective surfaces, and shields.

In an attempt to overcome these aforementioned problems, some light-generating devices have been manufactured with alternative light generating sources, such as light-emitting diodes (LEDs) which may be configured to radiate light at only desired wavelengths, thereby eliminating the need for special filters and generally reducing the amount of input power required to generate a desired output of radiation.

LEDs, however, emit light at a wide angle of dispersion, about 120°, which makes it difficult to focus the radiated light into the fiber optic wand. In order to capture the widely dispersed light, existing LED light-generating devices typically comprise special focusing reflectors and complicated designs that are required for housing the reflectors.

Yet another problem with existing devices is that they are not able to properly focus the light that is emitted from the LED or other light-generating source once it is directed out of the fiber optic wand. This is a problem because light emitted out of the fiber optic wand may create problems when it irradiates sensitive mouth tissues. Accordingly, it is desirable to focus the light only onto the light-curable compounds. Focusing the light onto the light-curable compounds can also be beneficial for reducing the duration of irradiation that is required to cure the light-curable compounds.

Accordingly, in view of the foregoing, there is currently a need in the art for improved devices for focusing light from light-generating sources for curing light-curable compounds during dental procedures.

SUMMARY OF PRESENTLY PREFERRED EMBODIMENTS

Briefly summarized, presently preferred embodiments of the present invention are directed to optical devices for focusing light which is directly emitted from light-generating sources of dental instruments for curing light-curable compounds.

According to one presently preferred embodiment, the optical devices of the invention comprise an aspheric lens and a transparent shield. The aspheric lens comprises a first end that is substantially flat and a second end that is curved. The curvature of this second end may comprise a hyperbolic curvature or an elliptical curvature and is configured for focusing light into a predetermined focus of illumination. According to another embodiment, the lens may comprise a hemispheric lens with a first end that is substantially flat and a second end comprising a hemispheric curvature.

According to the invention, the aspheric lens is configured to focus light emitting from a light-generating source such as a light-emitting diode (LED) of a light-generating dental device. The LED is preferably affixed to the end of an extension arm extending away from the light-generating dental device. The transparent shield, which is removably attachable to the extension arm, protects the aspheric lens from physical contact during use. The aspheric lens, according to one embodiment, is held securely in place by the transparent shield, with the flat end of the aspheric lens facing the LED and in close proximity to the LED.

The transparent shield is removably attachable to the extension arm by ridges and/or grooves that correspondently mate with ridges and/or grooves of the extension arm. The transparent shield is composed of a material composition that is suitable transparent for enabling light to pass therethrough. It will also be appreciated that the lens is composed of a material composition which is transparent. Suitable transparent materials for the lens and transparent shield include, but are not limited to, glass, aluminum dioxide, sapphire quartz, acrylic, polyacrylic, polypropylene and silicone.

According to one embodiment, the transparent shield comprises a conical shape having an apex, which may be used during the dental procedures to manipulate and press the light-curable compounds into a desired placement. After the dental procedure is completed, the transparent shield may be removed and replaced with a new transparent shield.

In some embodiments, in which the aspheric lens is composed of relatively inexpensive materials, such as common plastics, it may be desirable for the aspheric lens to be affixed to the transparent shield so that both the transparent shield and the aspheric lens may be replaced after use. In other embodiments, however, such as when the lens is composed of more expensive material compositions such as optical quartz, it may be desirable to affix the lens to the extension arm so that the transparent shield can be replaced without having to also replace the lens. When the lens is held in place by the extension arm, as well as with the other embodiments described herein, the optical devices of the invention may be broadly construed to include the extension arm and LED.

During use the LED emits light that is captured by the aspheric lens as a result of the proximity in which the aspheric lens is placed next to the LED. The light passing through the aspheric lens is focused by the aspheric lens into a desired focus of illumination that is desirable for polymerizing light-curable compounds while performing Class II dental restorations. According to one embodiment, the desired focus of illumination comprises a diameter of about 8 mm at a distance of about 3–5 mm from the apex of the transparent shield and about 3–10 mm away from the aspheric lens. However, the dimensions of the desired focus of illumination, or footprint, may vary to suit different needs and preferences.

It will be appreciated that one benefit of the invention is that the optical devices of the invention generally focus the light into a desired focus of illumination for irradiating Class II fillings. The optical devices of the invention also generally eliminate the need for fiber optic wands to direct the light from light-generating sources from within dental instruments to desired application sites. Yet another benefit of the invention is that it generally minimizes the loss of radiation energy due to filtering systems and dissipation, which occurs when light is not properly reflected and channeled into the fiber optic wand. It will be appreciated that these are improvements over the prior art light-generating dental devices currently used for curing light-curable compounds during dental procedures.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the optical devices of the invention will now be provided with specific reference to figures illustrating various embodiments of the optical devices. It will be appreciated that like structures will be provided with like reference designations.

Figure 1:
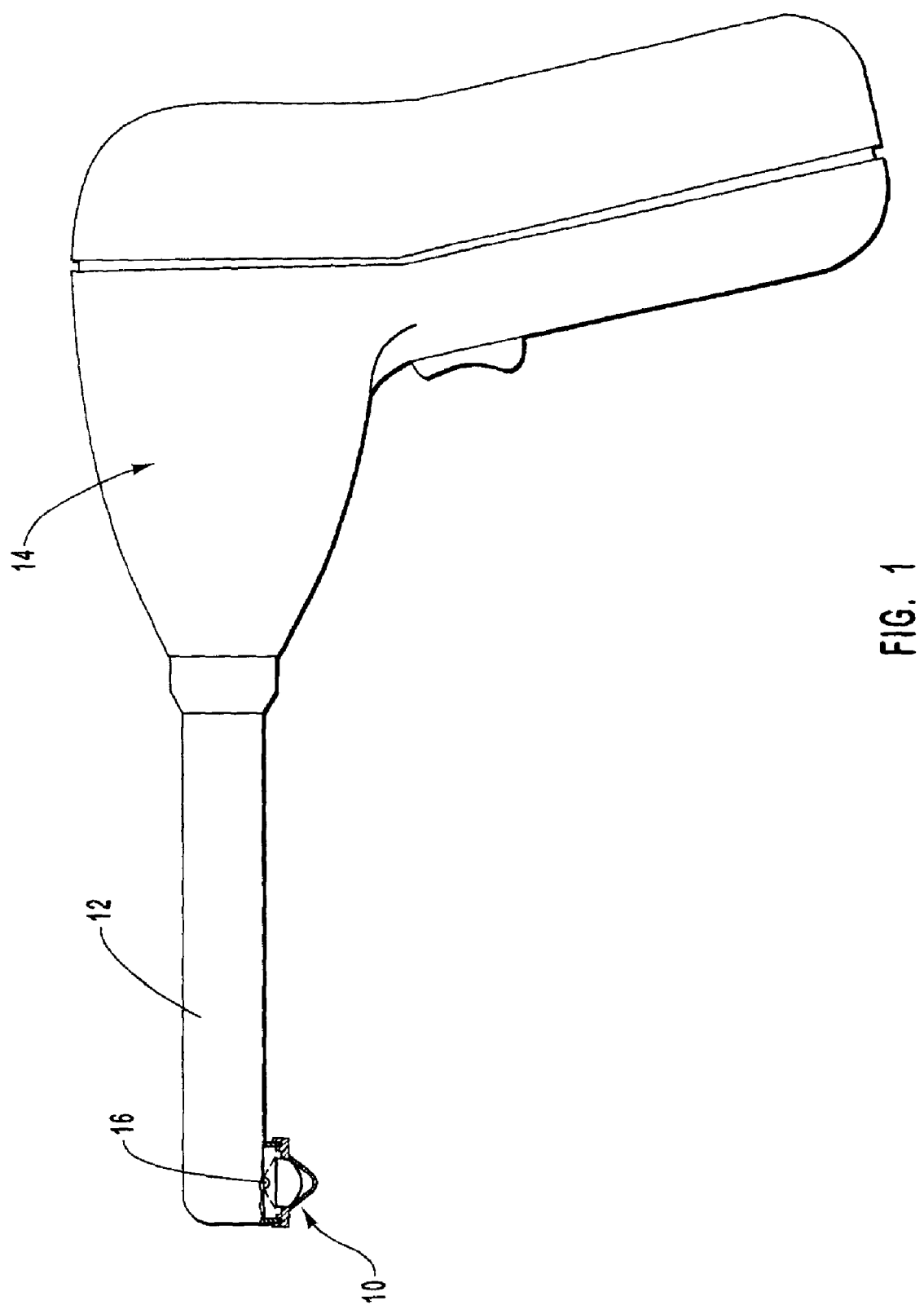
FIG. 1 illustrates a partial cross-sectional side view of one embodiment of a dental instrument that includes an extension arm with an LED and an optical device attached to the extension arm proximate the LED which includes an aspheric lens and a transparent shield.

Reference is first made to FIG. 1, which illustrates a partial cross-sectional view of one preferred embodiment of an optical device 10 of the invention. As shown, the optical device 10 is fixedly attached to an extension arm 12, which extends between optical device 10 and a dental instrument 14.

Dental instrument 14 may comprise any dental instrument or other device that is configured for generating light with a suitable wavelength for curing light-curable compounds, preferably within the range of about 400 nanometers to about 500 nanometers. According to one preferred embodiment, dental instrument 14 operates by supplying power to a light-emitting diode, such as LED 16. When LED 16 receives power supplied by dental instrument 14 then light, which is suitable for curing light-curable compounds, is generated and emitted by LED 16.

One problem with existing dental instruments is that the LED or other light-generating source is typically housed within the main body of the dental instrument, thereby requiring a fiber optic light wand to channel the light from the dental instrument to the dental application site where the light-curable compounds are located. This is a problem because the fiber optic light wand is unable to capture much of the light that is emitted from the LED. The light that is not captured increases the heat in the dental instrument and thus requires intricate cooling systems and devices to prevent overheating of the dental instrument. To overcome this problem, the present invention provides an optical device 10 which captures light at a remote location, away from the main body of the dental instrument 14, at the end of an extension arm 12, as shown. According to this embodiment, LED 16 generates light at the end of the extension arm 12, away from the main body of the dental instrument 14. It will be appreciated that separating LED 16 away from the main body of the dental instrument 14 is useful for minimizing the heat that is generated within the main body of dental instrument 14. Separating the optical device 10 away from the body of the dental instrument 14 is also ergonomically useful for enabling the dental practitioner to place the tip of the optical device 10 into the mouth of the patient during dental procedures.

Figure 2:
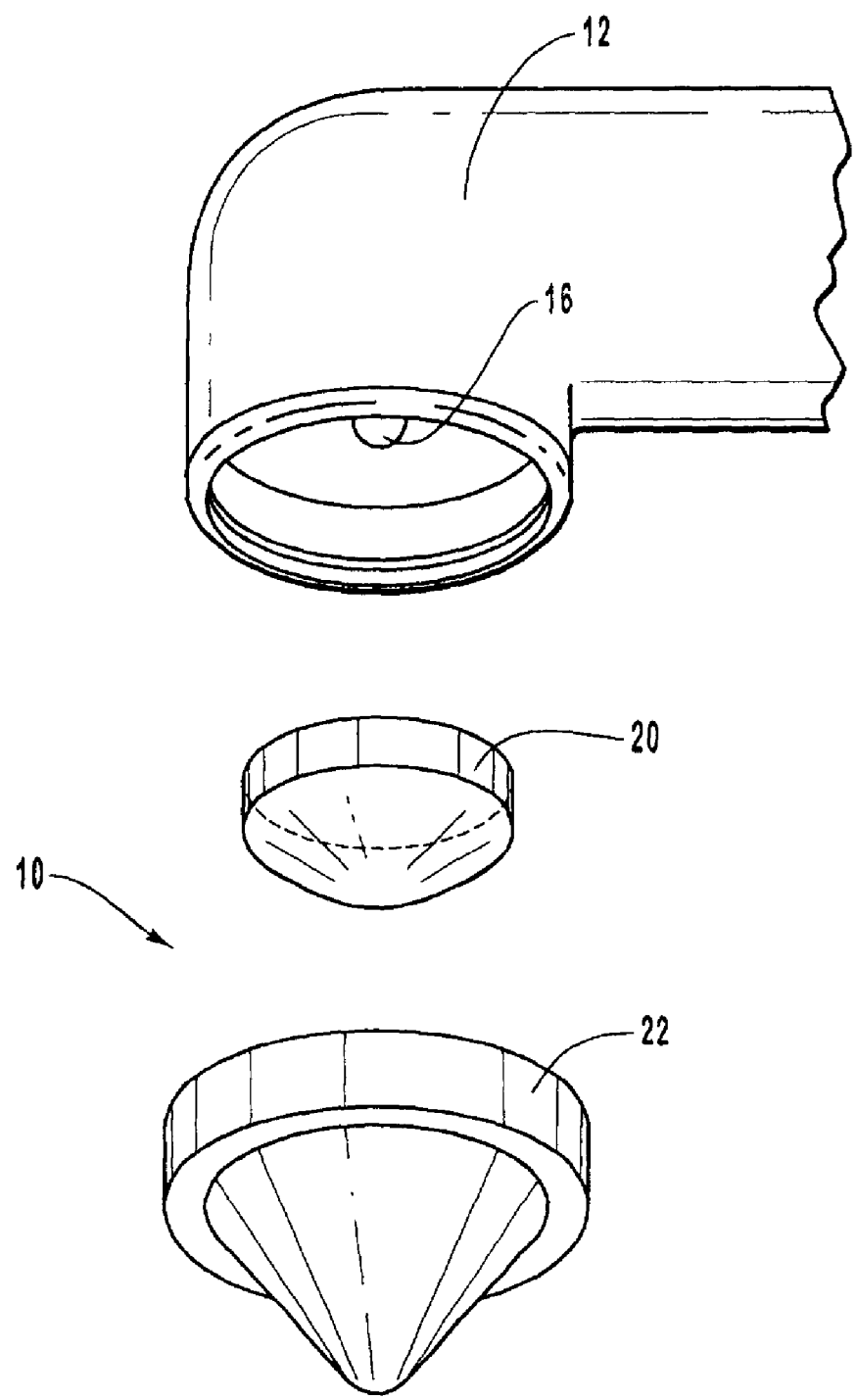
FIG. 2 illustrates a perspective view of one embodiment of the optical device of the invention that includes an aspheric lens and a transparent shield.

Turning to FIG. 2, it is shown that optical device 10 of the invention includes a lens 20 and a transparent shield 22. The lens 20 and the transparent shield 22 are preferably composed of a transparent material so as to enable light to pass therethrough. Suitable transparent materials include, but are not limited to, glass, aluminum dioxide, sapphire, quartz, acrylic, polyacrylic, polypropylene and silicone. The lens may also comprise a transilluminate lens that is color tinted for filtering out undesired radiant energy in particular color spectrums.

According to one preferred embodiment, the lens 20 is aspheric, as shown. The term "aspheric" is generally defined herein to include any curvature departing from a traditional spherical form. In particular, the term "aspheric" refers to any parabolic, hyperbolic, or ellipsoidal curvature.

Figure 3:
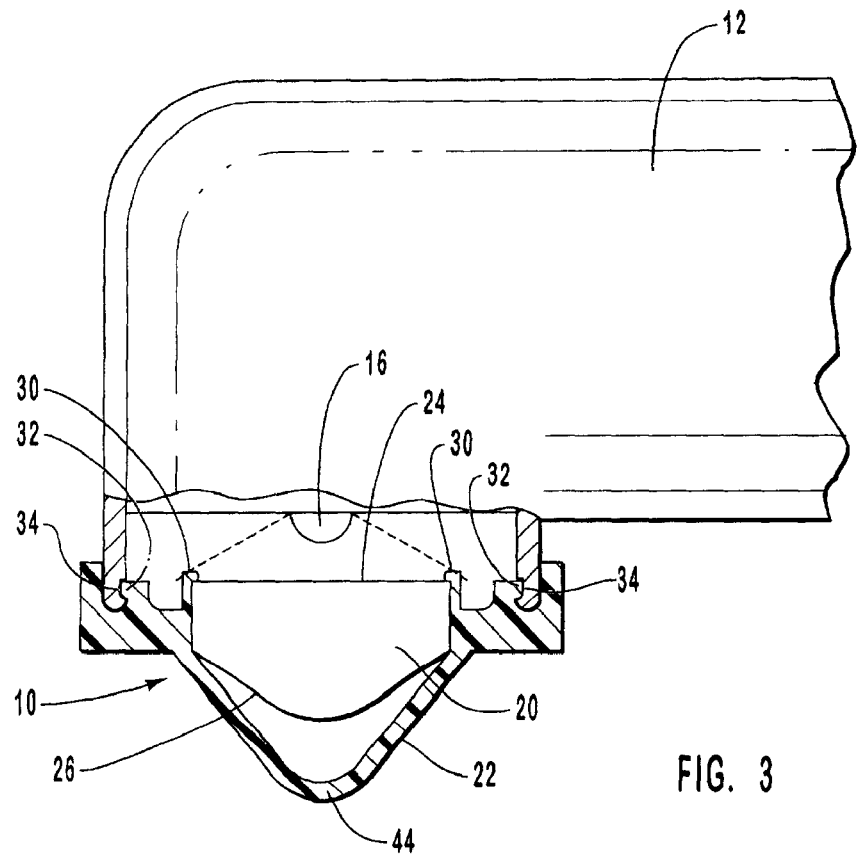
FIG. 3 illustrates a partial cross-sectional view of one embodiment of the optical device of the invention which includes an aspheric lens held securely in place by a transparent shield which is removably attachable to an extension arm having an LED in such a manner that the flat end of the aspheric lens is held facing and proximate the LED.
Figure 4:
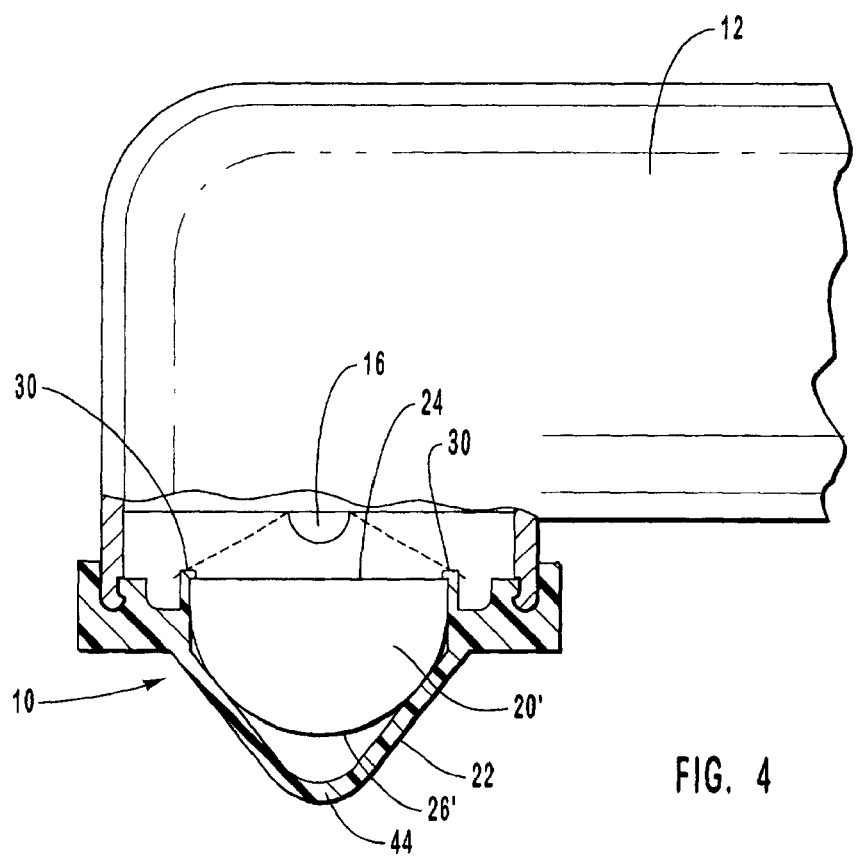
FIG. 4 illustrates a partial cross-sectional side view of one embodiment of the invention which includes a hemispheric lens held securely in place by a transparent shield which is removably attachable to an extension arm having an LED in such a manner that the flat end of the aspheric lens is held facing and proximate the LED.

Turning now to FIG. 3, it is shown how lens 20 comprises a first end 24 which is substantially flat and a second end 26, which is defined by a curvature. The curvature of the second end 26 is preferably aspheric comprising one of a hyperbolic curvature, a parabolic curvature, and an elliptical curvature. According to one alternative embodiment, the second end 26' of the lens 20' may also comprise a hemisphere or hemispheric curvature, as shown in FIG. 4. The function of the second end of the lens is generally to focus light into a predetermined focus of illumination.

According to one embodiment, optical device 10 also comprises means for securely holding the lens 20 in place so that the substantially flat first end 24 of the lens 20 is held in close proximity to, and facing, the LED 16, as shown in FIG. 3. This generally causes light emitting from the LED 16 to enter the substantially flat first end 24 of the lens 20. According to one embodiment, not shown, the LED 16 is ground flat so that the lens 20 can be placed directly against the flat surface of the LED 16. This alternative embodiment is useful for causing even more of the light emitted from the LED 16 to enter the lens 20.

It will be appreciated that transparent shield 22 comprises one suitable means for securely holding the lens 20 in place. In particular, the transparent shield 22 may hold the lens 20 securely in place by frictionally engaging the side surfaces of the lens 20 or alternatively the transparent shield 22 may be configured with clips 30, as shown, which wrap around and secure the lens 20 in place. The transparent shield also effectively protects the lens 20 from contact with foreign substances and materials during use.

Figure 5:
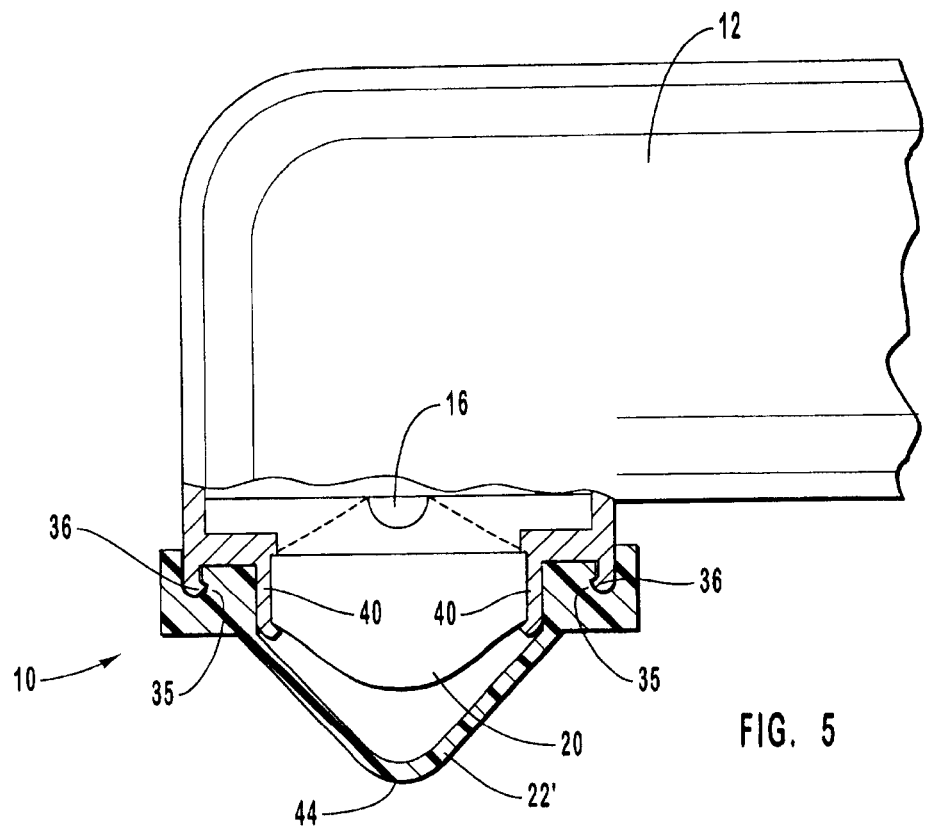
FIG. 5 illustrates a partial cross-sectional side view of one alternative embodiment of the optical device of the invention which includes an LED and an extension arm securely holding an aspheric lens in place, with a flat end of the aspheric lens facing and proximate the LED, and a transparent shield removably attachable to the end of the extension arm.

This embodiment shown in FIG. 3, with lens 20 held in place by transparent shield 22, is desirable when the lens 20 is manufactured with inexpensive materials such as plastics, thereby making the optical device 10 disposable and replaceable. According to one alternative embodiment, however, lens 20 may comprise material compositions that are more expensive, such as optical quartz, in which case it may be desirable for lens 20 to be fixedly attached to or at least securely held in place by extension arm 12. Such an embodiment is illustrated in FIG. 5. As shown, lens 20 is held securely in place by retaining walls 40 which extend down from extension arm 12 and which are configured for securely holding lens 20 in place. This embodiment is particularly useful for enabling the transparent shield 22 to be replaced without having to also replace the more expensive lens 20.

According to one preferred embodiment, transparent shield 22 is configured to be removably attachable to extension arm 12. As a matter of illustration, and not limitation, the transparent shield 22 may comprise ridges 32 that are configured for mating with corresponding grooves 34 in the extension arm 12, as shown in FIG. 3. According to another example, as shown in FIG. 5, the transparent shield 22' may also comprise grooves 35 that mate with corresponding ridges 36 of the extension arm 12. According to yet another embodiment, transparent shield 22' may be removably attachable to extension arm 12 with a friction fit (not shown) or with threads (not shown) for screwing the transparent shield 22' onto corresponding threads (not shown) of the extension arm 12.

Although the previous embodiments go into some detail regarding how the transparent shield 22 or 22' may be removably attached to the extension arm 12, it will be appreciated that the transparent shield 22 or 22' may also be fixedly attached to extension arm 12. By way of example and not limitation, the transparent shield 22 or 22' may be fixedly attached to extension arm 12 by welding or with adhesives.

According to embodiments in which the transparent shield 22 or 22' are fixedly attached to the extension arm 12, as well as with all other embodiments described herein, the optical device 10 may be broadly construed to include extension arm 12, as well as LED 16.

According to one preferred embodiment of the invention, light dispersed from the optical device 10 is focused by the lens 20 into a desired focus of illumination that is suitable for performing Class II restorations. Class II restorations are well known by those skilled in the art of dental restorations. According to one preferred embodiment, the desired focus of illumination, or footprint cast by the light, comprises a diameter of about 8 mm at a distance of about 3 mm to about 5 mm away from the apex 44 of the conical shaped transparent shield 22. Because the spacing between the lens 20 and the apex 44 of the transparent shield 22 or 22' may vary according to different embodiments, the distance between the aspheric lens 20 and the desired focus of illumination may also vary accordingly.

The distance between the second end 26 of lens 20 and the apex 44 is preferably within the range of about 3 mm to about 5 mm, such that the distance between the lens 20 and the desired focus of illumination is preferably within the range of about 3 mm and about 10 mm. It will be appreciated, however, that the dimensions and spacing of the optical device 10 may vary to accommodate various preferences and needs. For example, according to one alternative embodiment, which is not shown, the optical device 10 is configured so that the second end 26 of the aspheric lens 20 biases completely against the apex 44 of the transparent shield 22 or 22', with no space therebetween. This embodiment may be desirable for manufacturing purposes and for helping securely hold the lens within a desired placement.

Figure 6:
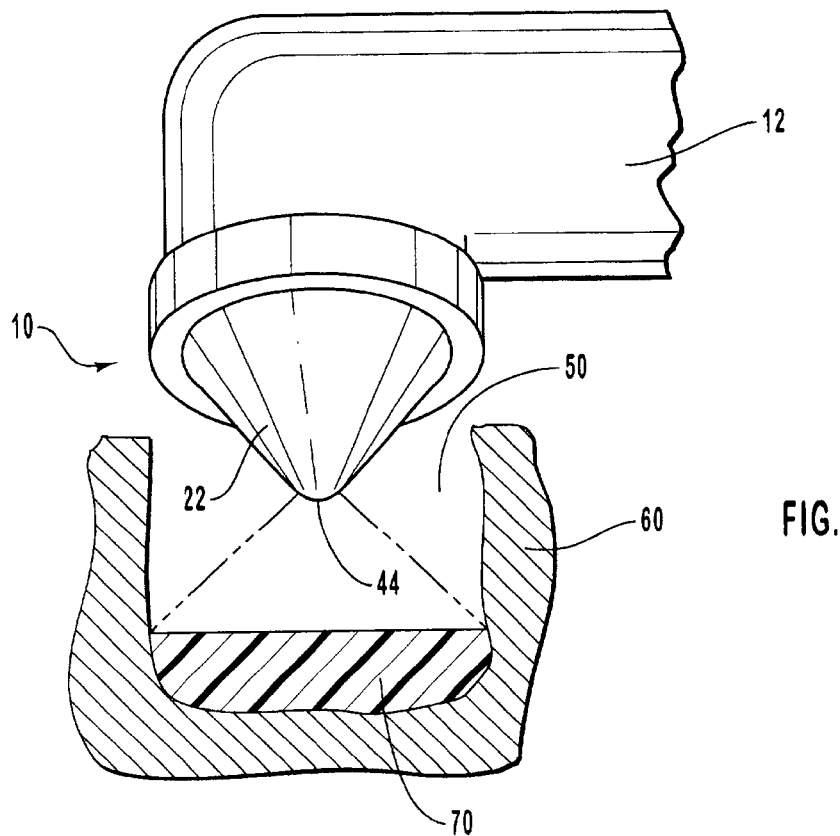
FIG. 6 illustrates one embodiment of the optical device of the invention and a cross-sectional view of a tooth, in which the transparent shield is conical having an apex which is inserted within the dental cavity preparation of a tooth, and in which light is being directed onto a light-curable compound within the dental cavity preparation.

Turning now to FIG. 6, it is shown how optical device 10 is configured for being inserted into the dental cavity preparation 50 of a tooth 60. Dental cavity preparation 50 may, as shown, be filled with a light-curable compound 70 that is cured when light radiation activates photosensitive components within the light-curable compounds, thereby enabling the light-curable compounds to polymerize and harden within the dental cavity preparation.

During use, the tip or apex 44 of the optical device 10 is inserted into the dental cavity preparation 50, and light is emitted for curing the light-curable compound 70. According to the invention, as described above, the light is focused by the optical device 10 into a focus of illumination having a diameter of about 8 mm at a distance of about 3 mm to about 5 mm away from the apex 44, which is desirable for curing Class II dental restorations. It will be appreciated, however, that the optical devices of the invention may be configured to create a focus of illumination of any dimension, suitable for curing any type of dental restoration.

Once the light-curable compound 70 has sufficiently hardened by the light that is directed out of the optical device, another layer of the light-curable compound 70 may be added to the dental cavity preparation 50 to be cured. This process may be repeated until the dental cavity preparation 50 is entirely filled.

One benefit of the optical devices of the invention, as described above, is that the optical devices of the invention generally focus light into a desired focus of illumination for irradiating Class II fillings. The optical devices of the invention also generally eliminate the need for fiber optic wands to direct the light from light-generating sources from within dental instruments to desired application sites. Yet another benefit of the invention is that it generally minimizes the loss of radiation energy due to filtering systems and dissipation, which occurs when light is not properly reflected and channeled into the fiber optic wand.

It will be appreciated that although specific examples have been provided above, regarding specific shapes and curvatures of the lens, the lens may comprise any desired shape for focusing light into a desired footprint.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed and desired to be secured by United States Letters Patent is:

1. An optical device for focusing light emitted from a light-generating source of a dental instrument, the optical device comprising:
   a lens having a first end that is substantially flat and a second end that is curved, wherein the substantially flat first end is configured for receiving light from the light-generating source, and wherein the curved second end is configured for focusing the light received by the first end;
   means for holding the first end of the lens adjacent to the light-generating source and for protecting the lens from contact; and
   wherein the means for holding and for protecting the lens comprise a transparent shield having means for removable attachment to the dental instrument so that it can be removed together with the lens and discarded after use.

2. An optical device as defined in claim 1, wherein the lens comprises at least one of glass, aluminum dioxide, sapphire, quartz, acrylic, polyacrylic, polypropylene, and silicone.

3. An optical device as defined in claim 1, wherein at least a portion of the second end of the lens has an aspheric curvature.

4. An optical device as defined in claim 3, wherein the aspheric curvature comprises at least one of a hyperbolic curvature, an elliptical curvature, and a parabolic curvature.

5. An optical device as defined in claim 1, wherein at least a portion of the second end has a hemispherical curvature.

6. An optical device as defined in claim 1, wherein the transparent shield protects the lens from making contact with light-curable compounds while allowing light from the light-generating source to pass through the shield.

7. An optical device as defined in claim 6, wherein the transparent shield comprises a conical portion having an apex.

8. An optical device as defined in claim 7, wherein the second end of the lens focuses light from the light-generating source into a column of light having a diameter of about 8 mm at a distance of about 3 mm to about 5 mm from the apex of the transparent shield.

9. An optical device as defined in claim 1, wherein the light-generating source comprises an LED.

10. In a dental curing apparatus comprised of a dental instrument having a main body for supplying electrical power, an extension arm attached at one end to said dental instrument, and through which electrical power is connectable to an LED light source, an improved optical device assembly connected to an opposite end of the extension arm, the optical device assembly comprising:
    a disposable assembly that may be removed and discarded after use on a patient, comprising:
      a lens positioned so as to receive light from the LED light source,
      said lens having a curved end that focuses the received light into a desired focus of illumination suitable for curing dental compounds within a patient's mouth, and
      a transparent shield which fits over and protects the lens, and into which the lens tits and is held, with the transparent shield in turn comprising means for removable attachment to the extension arm.

11. An optical device as defined in claim 10, wherein the lens and the transparent shield each comprise at least one of glass, aluminum dioxide, sapphire, quartz, acrylic, polyacrylic, polypropylene, and silicone.

12. An optical device as defined in claim 10, wherein the shape of the second end of the lens is at least one of hyperbolic, ellipsoidal, and parabolic.

13. An optical device as defined in claim 12, wherein the lens focuses the light entering the first end of the lens into a column of light having a diameter of about 8 mm at a distance of about 3 mm to about 10 mm away from the second end of the lens.

14. A dental curing apparatus comprising:
    a dental instrument comprised of a main body for supplying electrical power;
    an extension arm attached at one end to said dental instrument, and through which the electrical power is connectable to an LED light source; and
    an optical device assembly connected to an opposite end of the extension arm, the optical device assembly comprising:
      an LED light source connectable to the electrical power supplied from said main body of the dental instrument,
      a lens positioned so as to receive light from the LED light source, said lens having a curved end that focuses the received light into a desired focus of illumination suitable for curing dental compounds within a patient's mouth, and
      a rigid, conically shaped disposable transparent shield which fits over and protects the lens, and comprising means for removable attachment to the extension arm so that the transparent shield may be removed and discarded after use on a patient.

15. A dental curing apparatus as defined in claim 14, wherein the lens and the transparent shield comprise at least one of glass, aluminum dioxide, sapphire, quartz, acrylic, polyacrylic, polypropylene, and silicone.

16. A dental curing apparatus as defined in claim 14, wherein at least a portion of the second end of the lens is aspheric and is shaped so that it is formed into at least one of a hyperbolic, ellipsoidal, and parabolic shape.

17. A dental curing apparatus as defined in claim 14, wherein at least a portion of the second end of the lens is hemispherical.

18. A dental curing apparatus as defined in claim 14, further including a gap between the lens and LED light source such that they are not in abutting contact.

19. A dental curing apparatus as defined in claim 14, wherein the lens is held by the transparent shield so that the lens is removably attached to the extension arm along with the transparent shield.

20. A dental curing apparatus comprising:
   a dental instrument comprised of a main body for supplying electrical power;
   an extension arm attached at one end to said dental instrument, and through which the electrical power is connectable to an LED light source; and
   an optical device assembly connected to an opposite end of the extension arm, the optical device assembly comprising:
      an LED light source connectable to the electrical power supplied from said main body of the dental instrument,
      and a disposable assembly that may be removed and discarded after use on a patient, comprising:
         a lens positioned so as to receive light from the LED light source, said lens having a curved end that focuses the received light into a desired focus of illumination suitable for curing dental compounds within a patient's mouth, and
         a transparent shield which fits over and protects the lens, and into which the lens fits and is held, with the transparent shield in turn comprising a means for removable attachment to the extension arm.

21. A dental curing apparatus as defined in claim 20, wherein the lens comprises a first side that is substantially flat and an opposite side that is substantially curved.

22. A dental curing apparatus as defined in claim 21, wherein the substantially flat side of the lens is oriented toward the LED light source.

23. A dental curing apparatus as defined in claim 22, wherein the transparent shield holds the lens adjacent to the LED light source.

24. A dental curing light as defined in claim 23, wherein the lens and transparent shield comprise a plastic material.

25. A dental curing apparatus as defined in claim 20, wherein the means for removable attachment of the transparent shield to the extension arm comprises a threaded attachment.

26. A dental curing apparatus as defined in claim 20, wherein the transparent shield comprises a conical portion having an apex.

* * * * *

UNITED STATES PATENT AND TRADEMARK OFFICE
CERTIFICATE OF CORRECTION

| | | |
|---|---|---|
| PATENT NO. | : 7,106,523 B2 | Page 1 of 1 |
| APPLICATION NO. | : 10/044346 | |
| DATED | : September 12, 2006 | |
| INVENTOR(S) | : McLean et al. | |

It is certified that error appears in the above-identified patent and that said Letters Patent is hereby corrected as shown below:

Title page, Item (57)
Abstract, line 12, change "exists" to --exits--

Column 1
Line 43, after "compounds" add --.--

Column 5
After line 6, add the following omitted paragraph: --Another problem with prior art devices is that they are not able to properly focus the light that is emitted from the LED or other light-generating source once it is emitted by the light-generating source. This is a problem because unfocused light might irradiate and thereby irritate sensitive mouth tissues. Unfocused light can also increase the duration of time that is required to cure the light-curable compounds. The present invention overcomes these problems by providing an optical device 10 that is configured for focusing the light emitted by the light-generating source into a desired focus of illumination, as described herein.--

Column 8
Line 33, change "tits" to --fits--

Signed and Sealed this

Thirteenth Day of March, 2007

JON W. DUDAS
*Director of the United States Patent and Trademark Office*